United States Patent [19]
Sorokin et al.

[11] Patent Number: 6,025,526
[45] Date of Patent: Feb. 15, 2000

[54] SYNTHESIS OF SUBSTITUTED MERCAPTO-BENZALDEHYDES

[75] Inventors: Viktor D. Sorokin, Grand Island; Lawrence B. Fertel, Williamsville, both of N.Y.

[73] Assignee: Occidental Chemical Corporation, Dallas, Tex.

[21] Appl. No.: 09/248,053

[22] Filed: Feb. 10, 1999

[51] Int. Cl.$^7$ .................... C07C 319/02; C07C 321/26
[52] U.S. Cl. ....................... 568/41; 252/183.11
[58] Field of Search ............ 568/41; 252/183.11

[56] References Cited

U.S. PATENT DOCUMENTS

| | | | |
|---|---|---|---|
| 2,761,873 | 9/1956 | Gregory | 568/41 X |
| 4,187,319 | 2/1980 | Blohm et al. | 424/333 |
| 5,298,630 | 3/1994 | Kagano et al. | 568/41 X |

FOREIGN PATENT DOCUMENTS

| | | |
|---|---|---|
| 1-071852 | 3/1989 | Japan . |
| 64-071852 | 3/1989 | Japan . |
| 7-010829 | 1/1995 | Japan . |

OTHER PUBLICATIONS

Kagano et al., Chemical Abstracts, 124:55939, 1995.
English translation of JP 64–071,852, Mar. 16, 1989.

*Primary Examiner*—Fiona T. Powers
*Attorney, Agent, or Firm*—Ann E. Brookes; Richard D. Fuerle

[57] ABSTRACT

Disclosed is a composition of (1) a substituted benzaldehyde having the general formula

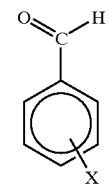

where X is a leaving group in the ortho or para position, (2) a mercaptide having the general formula MSR' in an amount about stoichiometric to about 20 mole % in excess of stoichiometric with the amount of said substituted benzaldehyde, where M is an alkali metal and R' is alkyl or haloalkyl from $C_1$ to $C_8$ or aryl, aralkyl, or alkyl from $C_6$ to $C_{12}$, (3) sufficient water to dissolve said mercaptide and MX, (4) about 0.1 to about 5 mole %, based on said substituted benzaldehyde, of a phase transfer catalyst, and (5) 0 to about 100 wt %, based on total composition weight, of a water-immiscible organic solvent. Heating the composition to a temperature between about room temperature and 100° C. results in the formation of a substituted mercapto-benzaldehyde.

19 Claims, No Drawings

SYNTHESIS OF SUBSTITUTED MERCAPTO-BENZALDEHYDES

BACKGROUND OF THE INVENTION

This invention relates to the synthesis of a substituted mercapto-benzaldehyde in an aqueous solution, with or without an organic solvent, by reacting a benzaldehyde having a leaving group with a mercaptide in the presence of a phase transfer catalyst. In particular, it relates to the synthesis of p-methyl-mercapto-benzaldehyde (PMMBAL) from p-chloro-benzaldehyde (PCBAL).

PMMBAL is an important compound which is useful as an intermediate in making drugs and agrochemicals. It can be synthesized by reacting PCBAL with an anhydrous alkali methyl mercaptide in an organic solvent with no water present. It is difficult to prepare the anhydrous methyl mercaptide, however, and the separation of the product from the salt byproduct requires filtration and extraction, followed by removal of an organic solvent and drying. The crude product also contains commercially unacceptable amounts of side products. Therefore, to obtain a product with high purity, a careful, time-consuming vacuum distillation is necessary.

SUMMARY OF THE INVENTION

We have discovered that a substituted mercapto-benzaldehyde can be made by reacting a benzaldehyde having a leaving group with a mercaptide in an aqueous solution using a phase transfer catalyst. While not required, a water-immiscible organic solvent can also be present. The salt byproduct dissolves in the water while the substituted mercapto-benzaldehyde product is either an immiscible oily phase or dissolves in the organic solvent if an organic solvent is present. Thus, the product can be easily separated from the salt byproduct. The process of this invention is simple and can be performed in a few hours. In producing PMMBAL, we have achieved isolated yields of 90 to 94% with purities higher than 99.5%.

DESCRIPTION OF THE PREFERRED EMBODIMENTS

The substrate for the process of this invention is a substituted benzaldehyde having the general formula:

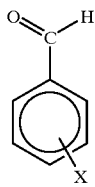

where X is a leaving group, that is, a group that can be replaced by the anion of the mercaptide. Any leaving group can be used in the process of this invention. Examples of leaving groups include halogens and $OSO_2R$, where R is halogen, $CF_3$, cyclic or acyclic alkyl from $C_1$ to $C_8$, or aryl, aralkyl, alkaryl from $C_6$ to $C_{12}$. Halogens are the preferred leaving groups and the most preferred leaving group is chlorine as those benzaldehydes are less expensive and some, such as PCBAL, are commercially available. The leaving group can be in the ortho or para position, but the para position is preferred as the products are more important commercially.

The mercaptide has the general formula MSR', where M is an alkali metal and R' is alkyl or haloalkyl from $C_1$ to $C_8$ or aryl, alkaryl, or aralkyl from $C_6$ to $C_{12}$. The M metal is preferably sodium or potassium and is most preferably sodium because some sodium mercaptides are commercially available. The R' group is preferably alkyl from $C_1$ to $C_4$ and is most preferably methyl because sodium methyl mercaptide (SMM) can produce PMMBAL. The amount of mercaptide should be about stoichiometric with the amount of substituted mercapto-benzaldehyde to about 20 mole % in excess of stoichiometric; less will leave unreacted benzaldehyde and more is unnecessary. Preferably, the amount of mercaptide is about 5 to about 15 mole % in excess of stoichiometric. The mercaptide is preferably dissolved in water as that increases the reaction rate. Some mercaptides, such as SMM, are sold commercially as an aqueous solution.

Sufficient water must be present in the process of this invention to dissolve the mercaptide and the salt byproduct. Excess water should be avoided as it increases the amount of material that must be processed and provides no additional benefit. Preferably, about 5 to about 80 wt % water can be used, based on the mercaptide weight.

While an organic solvent is optional and the reaction can be performed without an organic solvent, it is preferable to include a water-immiscible organic solvent if the product is soluble in water or remains as a solid during the reaction. If the product is a liquid, however, preferably no solvent is present. If a solvent is used, sufficient solvent should be present to dissolve the product. About 10 to about 100 wt %, based on the total composition weight, is usually adequate. Examples of suitable solvents include hydrocarbons and halogenated hydrocarbons such as benzotrifluoride, parachlorobenzotrifluoride, orthochlorotoluene, toluene, hexane, octane, chlorobenzene, xylenes, and ethers. Toluene and benzotrifluoride are preferred as they are inexpensive, the product dissolves well in them, and they separate easily from water.

The reaction is performed in the presence of about 0.1 to about 5 mole %, based on substrate weight, of a phase transfer catalyst. Less catalyst requires too much time for the reaction, and more catalyst is uneconomical. The preferred amount of catalyst is about 0.5 to about 1.5 mole %. Phase transfer catalysts are well known in the art. Examples include tetralkyl and tetraryl salts of ammonium and phosphonium, which have the general formula $(R'')_4NX'$ and $(R'')_4PX'$, respectively, where X' is OH, halide, hydrogen sulfate, or sulfonate and each R'' is independently selected from alkyl or aryl from $C_1$ to $C_{20}$. The preferred phase transfer catalysts are tetrabutyl ammonium bromide and tetrabutyl ammonium chloride as they have been found to work well. Examples of other phase transfer catalysts that can be used include tetrabutyl phosphonium bromide, tetrabutyl ammonium hydrogen sulfate, and methyltricaprylyl ammonium chloride.

In a preferred procedure, the mercaptide, water, catalyst, and optional organic solvent are mixed together and heated to a temperature between about room temperature and about 100° C.; the preferred temperature is about 40 to about 90° C. The substituted benzaldehyde is added to the heated mixture. It can be added as a solution in an organic solvent or as a solid, but it is preferable to melt it and add it as a liquid so that it can be metered in. In the absence of an organic solvent, the aqueous mercaptide solution and the catalyst can be mixed together and heated and the substituted benzaldehyde can be added to the heated solution of mercaptide as a solid or as a molten liquid. Because the reaction is exothermic, it is safer to add the substituted benzaldehyde last. The reaction is rapid and is complete in a few hours. The mixture is cooled down to room temperature, the two phases are separated, and, if a solvent is present, it is distilled off.

The following examples further illustrate this invention:

EXAMPLE 1 COMPARATIVE

Synthesis of PMMBAL from PCBAL and SMM using a $Bu_4NBr$ Catalyst

A 250 mL 4-necked round-bottom flask equipped with overhead stirrer, condenser, addition funnel, $N_2$ line, inlet tube, and heating mantle was charged with water (73.6 g, 4 mol) and toluene (80 mL). Sodium hydroxide pellets (12.1 g, 0.3 mol) were added portion-wise to the mixture and the mixture was stirred until the NaOH had completely dissolved. After cooling to room temperature, methyl mercaptan, $CH_3SH$, (16 g, 0.33 mol) was passed through the solution. A $BU_4NBr$ phase-transfer catalyst (3.7 g, 5 mol %) was added and the mixture was heated to 60° C. At this temperature, a solution of PCBAL (32 g, 0.227 mol) in toluene (60 mL) was added over 20 min. The mixture was stirred at 65 to 70° C. for 2.5 hours, then cooled to ambient temperature and poured into a separatory funnel. The upper brown layer was separated, washed with water (1×60 mL) and dried over $MgSO_4$. The $MgSO_4$ drying agent was removed and the solvent was stripped off under vacuum. The product, PMMBAL, was a clear yellowish oil. The yield was 31.7 g (92%) and the purity was 99.5% as determined by gas chromatography area % (GC).

EXAMPLE 2 COMPARATIVE

Preparation of PMMBAL in Water using a $Bu_4NBr$ Catalyst

Example 1 was repeated using 17 g (0.35 mol) methyl mercaptan and 2.2 g (3 mol %) $Bu_4NBr$. The mixture was heated to 70° C. and solid PCBAL (32 g, 0.227 mol) was added to the mixture portion-wise for 10 min. The resulting mixture was stirred at 70° C. for a period of 1 hour, cooled to ambient temperature, and poured into a separatory funnel. The bottom brown product layer was separated (36 g), washed with water (1×50 mL), and dried over $MgSO_4$ (5 g). After separating the $MgSO_4$, 32 g (92%) of yellow-brown product was obtained; the purity (GC) was 99.7%.

EXAMPLE 3

Preparation of PMMBAL in Water using a $Bu_4NBr$ Catalyst

Example 2 was repeated using 3.24 g (1 mol %) $Bu_4NBr$ and a 21 wt % aqueous solution of SMM (400.2 g, which contained 84 g/1.2 mol of SMM, made from 368 g water, 60 g NaOH pellets (1.5 mol), and 72 g $CH_3SH$ (1.5 mol)). The mixture was heated to 65° C. and molten PCBAL (140.5 g, 1 mol) was added over 10 min. The resulting mixture was stirred at 70° C. for 4 hours then cooled to ambient temperature and poured into a separatory funnel. The bottom yellow-brown product layer was separated (165 g), washed with water (1×150 mL), and dried over $MgSO_4$ (20 g). After removing the $MgSO_4$, the product was up-and-over distilled. A white-yellow clear oil was obtained. The yield was 140 g (92%), the bp was 110–111° C. @ 1.6 mm Hg, and the purity (GC) was 99.6%.

EXAMPLE 4

Preparation of PMMBAL in Water using a $Bu_4PBr$ Catalyst

Example 3 was repeated using 401.5 g of a 21 wt % aqueous solution of SMM (84 g/1.2 mol of SMM) and 3.39 g (1 mol %) $Bu_4PBr$. The mixture was heated to 70° C. and molten PCBAL (140.5 g, 1 mol) was added for 10 min. After stirring at 70° C. for 6 hours, the mixture was cooled to ambient temperature and poured into a separatory funnel. The bottom yellow-brown product layer was separated (158 g) and dried over $MgSO_4$ (20 g). After removing the $MgSO_4$, the crude PMMBAL was up-and-over distilled. A white-yellow clear oil was obtained. The yield was 136 g (89%), the bp was 108–109° C. @ 1.6 mm Hg, and the purity (GC) was 99.5%.

EXAMPLE 5

Preparation of PMMBAL using a $Bu_4NBr$ Catalyst

Example 4 was repeated using a commercial 21 wt % aqueous solution of SMM (Elf, France, 534.4 g, which contained 112 g (1.6 mol) of SMM) and 4.31 g (1 mol %) $Bu_4NBr$. The mixture was heated to 65° C. and molten PCBAL (188 g, 1.338 mol) was added for 25 min. After stirring at 70° C. for 4 hours, the mixture was cooled to ambient temperature and poured into a separatory funnel. The bottom yellow-brown product layer was separated (210 g), washed with water (200 mL), and dried over $MgSO_4$ (33 9). After removing the $MgSO_4$, the crude product (191 g) was up-and-over distilled. A white-yellow clear oil was obtained. The yield was 183 g (90%), the bp was 108–109° C. @ 1.6 mm Hg, and the purity (GC) was 99.7%.

EXAMPLE 6

Preparation of PMMBAL in Water using a Bu4NBr Catalyst Followed by Vacuum Distillation Example 5 was repeated using 414.6 g of a 21 wt % aqueous solution of SMM (87 g/1.24 mol of SMM) and 3.36 g (10 mmol, 1 mole %) $Bu_4NBr$. The mixture was heated to 70° C. and molten PCBAL (146.7 g, 1.04 mol) was added for 20 min. After stirring at 70° C. for 6 hours, the mixture was cooled to ambient temperature and poured into a separatory funnel. The bottom yellow product layer was separated (157 g) and this wet material was up-and-over distilled. The white-yellow clear oil was obtained. The yield was 133.5 g (84.5%), the bp was 118–120° C. @ 1.5 mm Hg, and the purity (GC) was 99.8%.

EXAMPLE 7

Preparation of PMMBAL in Water using a $Bu_1NHSO_4$ Catalyst

Example 6 was repeated using 50 g of a 21 wt % aqueous solution of SMM (10.5 g/0,15 mol of SMM) and 0.438 g (1.29 mmol, 1 mole %) $Bu_4NHSO_4$. The mixture was heated to 70° C. and molten PCBAL (18.1 g, 0.129 mol) was added for 5 min. After stirring at 70° C. for 7 hours, the mixture was cooled to ambient temperature and poured into a separatory funnel. The bottom yellow product layer was separated (18.82 g) and dried over $MgSO_4$ (3 g). After removing the $MgSO_4$, 17.9 g (91%) of clear bright yellow oil with a purity (GC) of 99.3% was obtained.

EXAMPLE 8

Preparation of PMMBAL in Water using "Aliguat 336" as a Catalyst

Example 7 was repeated using 51 g of a 21 wt % aqueous solution of SMM (10.71 g/0.153 mol of SMM) and 0.55 g (1.36 mmol, 1 mol %) methyltricaprylyl ammonium chloride, sold by Aldrich as "Aliquat 336." The mixture was heated to 70° C. and molten PCBAL (18.69 g, 0.132 mol) was added for 5 min. After stirring at 70° C. for 6 hours, the mixture was cooled to ambient temperature and poured into a separatory funnel. The bottom yellow product layer was separated (19.32 g) and dried over MgSO$_4$ (3 g). After removing the MgSO$_4$, 18.53 g (92%) of clear bright yellow oil with a purity (GC) of 99.4% was obtained.

We claim:

1. A method of making a substituted mercapto-benzaldehyde by reacting a substituted benzaldehyde with a mercaptide comprising
   (A) preparing a composition which comprises
     (1) a mercaptide having the general formula MSR', where M is an alkali metal and R' is alkyl or haloalkyl from $C_1$ to $C_8$ or aryl, alkaryl, or aralkyl from $C_6$ to $C_{12}$, in an amount about stoichiometric to about 20 mole % in excess of stoichiometric with the amount of said substituted benzaldehyde to be reacted; and
     (2) sufficient water to dissolve said mercaptide and MX;
     (3) about 0.1 to about 5 mole %, based on said substituted benzaldehyde, of a phase transfer catalyst; and
     (4) 0 to about 100 wt %, based on total composition weight, of a water-immiscible organic solvent;
   (B) heating said composition to a temperature between about room temperature and about 100° C.;
   (C) melting a solid substituted benzaldehyde having the general formula:

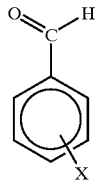

where X is a leaving group in the ortho or para position; and
   (D) metering said melted substituted benzaldehyde into said composition.

2. A method according to claim 1 wherein said leaving group is halogen or has the formula OSO$_2$R where R is halogen, CF$_3$, cyclic or acyclic alkyl from $C_1$ to $C_8$, or aryl, aralkyl, or aralkyl from $C_6$ to $C_{12}$.

3. A method according to claim 1 wherein X is halogen.

4. A method according to claim 3 wherein X is chlorine.

5. A method according to claim 1 wherein X is in the para position.

6. A method according to claim 1 wherein M is sodium or potassium.

7. A method according to claim 1 wherein R' is methyl.

8. A method according to claim 1 wherein the amount of water is about 5 to about 80 wt %, based on mercaptide weight.

9. A method according to claim 1 wherein said phase transfer catalyst has the general formula (R")$_4$NX' or (R")$_4$PX', where X' is OH, halide, hydrogen sulfate, or sulfonate and each R" is independently selected from alkyl or aryl from $C_1$ to $C_{20}$.

10. A method according to claim 1 wherein no organic solvent is present.

11. A method according to claim 1 wherein about 10 to about 100 wt %, based on total method weight, of a water-immiscible organic solvent is present.

12. A method according to claim 11 wherein said water-immiscible organic solvent is toluene or benzotrifluoride.

13. A method according to claim 10 wherein said substituted mercapto-benzaldehyde is a liquid that forms a separate phase from said water.

14. A product composition made according to the method of claim 1.

15. A method of making a substituted mercapto-benzaldehyde by reacting a substituted benzaldehyde with a mercaptide comprising
   (A) preparing a composition which comprises
     (1) a mercaptide having the general formula MSR', where M is Na or K and R' is alkyl or from $C_1$ to $C_4$, in an amount stoichiometric to about 5 to about 15 mole % in excess of stoichiometric with the amount of said substituted benzaldehyde to be reacted;
     (2) about 5 to about 80 wt % water;
     (3) about 0.5 to about 1.5 mole %, based on said substituted benzaldehyde, of a phase transfer catalyst; and
     (4) 0 to 100 wt %, based on total composition weight, of a water-immiscible organic solvent;
   (B) heating said composition to a temperature between about 40 and about 90° C.;
   (C) melting a solid substituted benzaldehyde having the general formula:

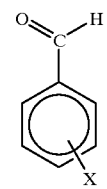

where X is halogen; and
   (D) metering said melted substituted benzaldehyde into said composition.

16. A product composition made according to the method of claim 15.

17. A method of making p-methyl-mercapto-benzaldehyde by reacting p-chloro-benzaldehyde with sodium methyl mercaptide comprising
   (A) preparing a composition which comprises
     (1) sodium methyl mercaptide in an amount about 5 to about 15 mole % in excess of stoichiometric with the amount of said p-chloro-benzaldehyde to be reacted;
     (2) about 5 to about 80 wt % water, based on the weight of said sodium methyl mercaptide; and
     (3) about 0.5 to about 1.5 mole % of a phase transfer catalyst;
   (B) heating said composition to about 40 to about 90° C.;
   (C) melting said p-chloro-benzaldehyde; and
   (D) metering said melted p-chloro-benzaldehyde into said composition.

18. A method according to claim 17 wherein said phase transfer catalyst is tetrabutylammonium bromide, tetrabutylammonium chloride, tetrabutyl phosphonium bromide, tetrabutyl ammonium hydrogen sulfate, or methyltricaprylyl ammonium chloride.

19. A product composition made according to the method of claim 18.

* * * * *